United States Patent
Petignaud

(10) Patent No.: US 8,226,231 B2
(45) Date of Patent: Jul. 24, 2012

(54) SYSTEMS AND METHODS FOR IMPROVING THE RECEPTIVENESS OF A PERSON TO A TRAINING SESSION FOR IMPROVING VISUAL PERCEPTION

(75) Inventor: Cecile Petignaud, Charenton le Pont (FR)

(73) Assignee: Essilor International (Compagnie General d'Optique), Charenton le Pont (FR)

(*) Notice: Subject to any disclaimer, the term of this patent is extended or adjusted under 35 U.S.C. 154(b) by 202 days.

(21) Appl. No.: 12/452,421

(22) PCT Filed: Jun. 26, 2008

(86) PCT No.: PCT/EP2008/058211
§ 371 (c)(1), (2), (4) Date: Dec. 28, 2009

(87) PCT Pub. No.: WO2009/000902
PCT Pub. Date: Dec. 31, 2008

(65) Prior Publication Data
US 2010/0134758 A1    Jun. 3, 2010

(30) Foreign Application Priority Data
Jun. 27, 2007 (EP) .................................... 07301160

(51) Int. Cl.
*A61B 3/00* (2006.01)
*A61B 3/02* (2006.01)

(52) U.S. Cl. ................ 351/203; 351/246; 351/239
(58) Field of Classification Search ........... 351/200–246
See application file for complete search history.

(56) References Cited

U.S. PATENT DOCUMENTS

| 5,589,897 A | 12/1996 | Sinclair et al. |
|---|---|---|
| 6,007,197 A | 12/1999 | Locatelli |
| 6,876,758 B1 | 4/2005 | Polat et al. |
| 7,556,381 B2 * | 7/2009 | Kelch et al. .................. 351/246 |
| 2003/0109800 A1 | 6/2003 | Polat |

FOREIGN PATENT DOCUMENTS

| EP | 1 262 815 | 4/2002 |
|---|---|---|
| WO | WO 02/09579 | 2/2002 |
| WO | WO 2005/044096 | 5/2005 |
| WO | WO 2006/025056 | 3/2006 |
| WO | WO 2007/043047 | 4/2007 |

* cited by examiner

*Primary Examiner* — Mohammed Hasan
(74) *Attorney, Agent, or Firm* — Cozen O'Connor

(57) ABSTRACT

A method to improve the receptiveness of a person to a training session of the human visual system where at least one visual stimuli arrangement is provided to the person and where means are provided so that the high order aberrations of the system consisting of the combination of said means and the eye of the person is lower than the high order aberrations of the eye of the person. The method to improve deficiencies, inefficiencies or both in neuronal interaction comprising preceding improvement method. A system such as a lens system, an artificial pupil or a clipable lens adapted for said methods. Related computer program product and computer-readable medium.

25 Claims, 2 Drawing Sheets

SYSTEMS AND METHODS FOR IMPROVING THE RECEPTIVENESS OF A PERSON TO A TRAINING SESSION FOR IMPROVING VISUAL PERCEPTION

RELATED APPLICATIONS

This is a U.S. national stage of application No. PCT/EP2008/058211, filed on Jun. 26, 2008.

This application claims the priority of European patent application no. 07301160.3 filed Jun. 27, 2007, the entire content of which is hereby incorporated by reference.

FIELD OF THE INVENTION

The invention relates generally to the field of vision improvement and, more specifically, improving the receptiveness of a person to a training session for improving visual perception and acuity abilities, and improving the visual perception process and neural performance of a person.

BACKGROUND OF THE INVENTION

Human eyesight is a product of two separate processes that work together to form images for a person to "see". One of these processes, herein referred to as the physical component, concerns the physical structure of the various elements of the eye and how incoming light is manipulated and processed by the eye. Defects in the shape of the cornea, the retinal wall, or the optic nerve can impair or destroy the functionality of a person's eye and thus impair or eliminate the ability to perceive images. Fortunately, defects in the cornea of a person can be corrected through the use of glasses, contacts, or surgery such as laser keratotomy. Likewise, defects in the retina of a person might be often repairable by surgery.

The second process involved in allowing humans to see images is herein referred to as the neurological component. This component concerns neural processing in the brain and how the brain analyzes information sent from the eyes to produce an image. A person can likewise have a number of defects in this component of the visual process, such as reduced visual acuity, reduced sensitivity for spatial contrast, reduced vernier acuity, spatial distortion, abnormal spatial interactions and impaired contour detection.

The physical component and the neurological component work together to form images that a person sees, or more precisely, that a person perceives.

A visual system is classically described as a hierarchy of visual processing stages (though recent views emphasize backward projections), starting from light detection and transduction in the eye (i.e. photoreceptors) through several stages of spatial integration, each stage forming receptive fields of increasing complexity. An important stage in image analysis, in the primary visual cortex, includes receptive fields (units) that are sensitive to image contrast that varies in a specific direction (orientation selectivity) on a specific scale (size selectivity). Human contrast sensitivity is best described by the aggregate response of these units (filters).

Recent research (psychophysics, physiology) points to spatial interactions between oriented receptive fields as an important factor in modulating activity of the corresponding neuronal units. Local contrast sensitivity can be increased or decreased depending on the light distribution within neighboring locations. More specifically, facilitation of oriented contrast detection is obtained by presenting for example a target flanked by collinear, high contrast stimuli at an optimal distance. Levels of neuronal suppression can be obtained by presenting the target with more proximal co-oriented flankers.

Responses of individual neurons to repeated presentations of the same stimulus are highly variable (noisy). Noise may impose a fundamental limit on the reliable detection and discrimination of visual signals by individual cortical neurons. Neural interactions determine the sensitivity for contrast at each spatial frequency, and the combinations of neural activities derive an individual's contrast sensitivity function (CSF). The brain pools responses across many neurons to average out noisy activity of single cells, thus improving signal-to-noise ratio, leading to substantially improved visual performance.

As for an example, the studies of Uri Polat et al. have shown that the noise of individual cortical neurons can be brought under experimental control by appropriate choice of visual stimulus conditions.

A method for identifying deficiencies and/or inefficiencies in neuronal interaction of a person's visual cortex and possibly train this person, has been disclosed in U.S. Pat. No. 6,876,758 and U.S. Pat. No. 7,007,912 in the name of U. Polat. Studies of U. Polat et al. enclose following references:

Polat, Uri and Sagi, Dov, "Plasticity of Spatial Interactions in Early Vision" Department of Neurobiology, Brain Research, the Weizmann Institute of Science, Rehovot 76100 Israel, Levi, Dennis and Polat, Uri "Neural Plasticity in Adults with Amblyopia", Proc. Natl. Acad. Sci. USA, Neurobiology, vol. 93, pp 6830-6834, February 1996, Polat, Uri, "Functional Architecture of Long-range Perceptual Interactions" Spatial Vision, vol. 12, no 2, pp 143-162, 1999.

As for an example, a method called NeuroVision has been developed, based on these principles and commercialized by the Company Neurovision Inc. (Singapore) to offer eye correction training session.

A typical building block of the suggested visual stimulations is the Gabor patch, which efficiently activates and matches the shape of receptive field in the visual cortex.

Polat and colleagues have demonstrated that contrast sensitivity of adult human subjects at low levels can be increased by a factor of 2 through specific control of the Gabor patches parameters. This stimulation-control technique is called "Lateral Masking", where collinearly-oriented flanking Gabors are displayed in addition to the target Gabor image.

In the first stage of a training session overview, the subject is exposed to a set of visual perception tasks, aimed to analyze and identify each subject's neural inefficiencies. The images are for example images presented to the patient on a monitor screen. The patient has to perform visual tasks indicating whether he/she sees a target arrangement. The indications may be made by means of a computer mouse.

A training system may analyze subject's performance. Based on said analysis, training plan can be initialized, and subject specificity can be achieved by administering patient-specific stimuli in a controlled environment. The stimuli parameters can be automatically tailored to each subject's needs; among these parameters are spatial frequencies, spatial arrangement of the Gabor patches, contrast level, orientation (local and global), tasks order, context, timing.

Each session may be designed to train, directly and selectively, those functions in the visual cortex that were diagnosed to be ineffective. At each session an algorithm may analyze the patient's responses and accordingly adjusts the level of visual difficulty to the range most effective for further improvement. Between sessions, the progress of the patient may be measured and taken into account by the algorithm for the next therapeutic session. Thus, for each subject an individual training schedule may be designed, and adapted during the training session, based on the initial state of visual performance, severity of dysfunction and progress in training.

As for an example, the training session is applied in successive 30-minute sessions, administered 2-3 times a week, a total of approximately 20-30 sessions. Every 5 sessions, subject's visual acuity may be tested in order to continuously monitor subject's progress.

A training system is usually a software-based, interactive system tailored and continuously adaptive to the individual patient's learning and improvement. The Internet can be used as a distribution media, which allows providing this personalized interactive service to a practically unlimited number of training locations.

During each training session, the patient at the clinic/investigative site can be exposed to visual images displayed on a computer monitor. The patient can interactively communicate with the computer using for example a mouse. During the session, some data that reflects patient's performance can be recorded. At the end of the session, this data can be sent to a central server. Algorithmic software, running on the server, can analyze the patient's performance and progress and can generate the parameters for the next training session.

Although clinical tests have shown that about 70 percent of the users of training such as a Neurovision training system and method have improved their eye conditions, the inventors have noticed that the efficiency of said method is not always optimal.

Accordingly there remains a need for improving the receptiveness of a person to a training session of the human visual system where visual stimuli arrangements are provided to the person.

A non-limiting example of such training session is a NeuroVision training session where arrangements are designed to modify levels of neuronal facilitation and/or levels of neuronal suppression in the person's visual cortex.

SUMMARY OF THE INVENTION

One object of the present invention is to improve the receptiveness of a person to a training session of the human visual system where a plurality of visual stimuli arrangements is provided to the person, in order to enhance its efficiency.

This object is obtained according to the invention by a method improve the receptiveness of a person to a training session of the human visual system where at least one visual stimuli arrangement is provided to the person and where means are provided so that the high order aberrations of the system consisting of the combination of said means and the eye of the person is lower than the high order aberrations of the eye of the person.

The method of improving the receptiveness of a person to training session is not a therapeutic method.

The training session includes for example providing to the person one or more sessions for improving deficiencies, inefficiencies, or both, in neuronal interaction of the person's visual cortex.

Ophthalmologists or optometrists routinely improve visual acuity by correcting refracting errors in terms of sphere, cylinder and axis. Said refractive errors are low order aberrations.

High order aberrations are refractive errors beyond sphere and cylinder. They are important because it has been recently stated that poor vision may occur due to uncorrected high order aberrations.

Surprisingly the inventors have observed that providing means to a person so that the high order aberrations of the system consisting of the combination of said means and the eye of the person is lower than the high order aberrations of the eye of the person makes possible to improve the receptiveness of a person to the mentioned training session, such as for example a NeuroVision training session. They have demonstrated that using said receptiveness improving method, it is possible to train with success persons where the training session previously failed, or to increase the success of the training session for persons where the training session previously encountered success.

According to further embodiments which can be considered alone or in combination:

- at least one visual stimuli arrangement is designed to modify levels of neuronal facilitation and/or levels of neuronal suppression in the person's visual cortex;
- the method comprises following steps:
  (a) measuring aberrations of at least one eye of the person;
  (b) calculating a parameter which is characteristic of the high order aberrations of an optical system with the data of step (a);
  (c) providing means so that the high order aberrations of the system consisting of the combination of said means and the eye of the person is lower than the high order aberrations of the eye of the person;
- the parameter which is characteristic of the high order aberrations of an optical system is chosen in the list consisting of the high order aberrations RMS (Root Mean Square) value, the Strehl Ratio, the Pupil Ratio;
- the parameter which is characteristic of the high order aberrations of an optical system is the high order aberrations RMS (Root Mean Square) value, the value of this parameter for the system consisting of the combination of the means and the eye of the person is lower than the value of this parameter for the eye of the person;
- aberrations are calculated using Zernike polynomials analysis and the high order aberrations RMS is calculated for orders equal or greater to the third order;
- the RMS value of the system consisting of means of step (c) combined with the eye of the person is equal or less to 0.14 µm, and for example equal or less to 0.10 µm for a normalized pupil of 3.5 mm;
- means which are provided, for example means of step (c), is an optical system to be worn by the person to be trained;
- the optical system is a two zones lens (1) comprising a central zone (2) and a surrounding zone (3), where the surrounding zone (3) is adapted to the vision parameters of the person and the central zone (2) is also adapted to the vision parameters of the person and the high order aberrations of the system consisting of the combination of the central zone (2) of the lens (1) and the eye of the person is lower than the high order aberrations of the eye of the person;
- the optical system consists of a first lens which is adapted to the vision parameters of the person and a second lens which is designed so that the high order aberrations of the system consisting of the combination of the first and second lens of the lens system and the eye of the person is lower than the high order aberrations of the eye of the person;
- the second lens is clipable on the first lens;
- optical system consists of a lens which is adapted to the vision parameters of the person and an artificial pupil disposed on said lens;

each visual stimuli arrangement comprises one or more target images each flanked by a pair of flanking images.

Aberrometers, that are wavefront sensors for the specific measurement of the eye, are instruments designed to measure the wavefront of the eye, including sphere, cylinder and the high-order aberrations.

Using such instrument makes possible to measure and/or calculate the aberrations level of an eye and separate the contribution of low and high order aberrations.

Among the parameters known in the state of the art which are characteristic of the high order aberrations of an optical system are non limiting following: "high order aberrations RMS (Root Mean Square) value", "Strehl Ratio", "Pupil Ratio".

It is then possible to calculate those using aberrometers measurement of an eye.

"High order aberrations Root Mean Square" is usually written as HOA RMS or as HO_RMS in the present text; its unit is usually micrometer (μm).

In absence of aberrations, the intensity is a maximum at a Gaussian image point. "Strehl Ratio" is used to characterize aberrations: it is the ratio of the intensity at the Gaussian image point (the origin of the reference sphere is the point of maximum intensity in the observation plane) in the presence of aberrations, divided by the intensity that would be obtained if no aberration were present.

"Pupil Ratio", also called "pupil fraction" is based on evaluation of the fraction of the pupil area for which the aberrations map is reasonably good quality (see for example: "Estimating Visual Quality from Wavefront Aberration Measurements", by Xu Cheng et al. —Journal of Refractive Surgery, Vol. 19, pages 579 to 584; see also Glenn Fry Award Lecture 2002, "Wavefront Sensing, Ideal Corrections, and Visual Performance", by RAYMOND A. APPLEGATE; VOL. 81, NO. 3, PP. 167-177—OPTOMETRY AND VISION SCIENCE Copyright© 2004 American Academy of Optometry, namely "The whole pupil fraction varies between zero and one and is calculated by determining the fraction of the total pupil area with a wave aberration of less than a predetermined fixed amount", on page 176.)

The invention relates also to a method for identifying deficiencies, inefficiencies, or both, in neuronal interactions of a person's visual cortex, the method comprising:

(a) providing means so that the high order aberrations of the system consisting of the combination of said means and the eye of the person is lower than the high order aberrations of the eye of the person;

(b) providing to the person visual stimuli comprising an arrangement of one or more target images where the arrangement is designed to induce a level of neuronal facilitation and/or levels of neuronal suppression in the person's visual cortex;

(c) receiving from the person a response to the visual stimuli provided in step (b) the response indicating detection or discrimination by the person of the one or more target images; and (d) providing further visual stimuli to the person based at least in part on the response received in step (c) the further visual stimuli comprising a further arrangement of one or more target images designed to induce a different level of facilitation and/or levels of neuronal suppression in the person's visual cortex than the visual stimuli provided in step (b); said step (b)-(d) being repeated until responses to a sufficient number of facilitation and/or levels of neuronal suppression levels are received from the person such that deficiencies, inefficiencies, or both, in neuronal interactions of the person's visual cortex may be identified by comparing a function of the person's responses to a normative response function of persons without known vision deficiencies.

According to an embodiment of preceding method for identifying deficiencies, inefficiencies, or both, in neuronal interactions of a person's visual cortex, step (a) comprises following substeps:

(a1) measuring aberrations of at least one eye of the person;

(a2) calculating a parameter which is characteristic of the high order aberrations of an optical system with the data of step (a1);

(a3) providing means so that the high order aberrations of the system consisting of the combination of said means and the eye of the person is lower than the high order aberrations of the eye of the person.

According to another embodiment the method further comprises providing to the person one or more training sessions of the human visual system including:

(e) providing to the person visual stimuli arrangements, each arrangement comprising one or more target images designed to modify levels of neuronal facilitation and/or levels of neuronal suppression in the person's visual cortex;

(f) receiving responses from the person indicating detection or discrimination of the target images in the respective visual stimuli arrangements;

(g) comparing the person's responses with prior response received from the person to the same or similar visual stimuli arrangements; and (h) repeating steps (e)-(g), the visual stimuli arrangements provided in each step (e) based at least partly on results of the preceding comparison step (g) until a sufficient number of responses are received from the person so that improvement in deficiencies, inefficiencies, or both, in neuronal interactions of the person's visual cortex may be identified by comparing a function of the person's responses to a normative response function of persons without known vision deficiencies.

Furthermore, the target images of steps (b) or (d) or (e) may be each flanked by one or more flanking images of similar configuration as the respective target image, and the arrangement may comprise a parameter of the one or more target images and the respective flanking images.

It has to be understood that the different embodiments of the previously mentioned method to improve the receptiveness of a person to a training session of the human visual system may be included in the present methods for identifying deficiencies, inefficiencies, or both, in neuronal interactions of a person's visual cortex and/or training the human visual system.

The invention relates also to a system to improve the receptiveness of a person to a training session of the human visual system where at least one visual stimuli arrangement is provided to the person, and where the system comprises means designed so that the high order aberrations of the system consisting of the combination of the means and the eye of the person is lower than the high order aberrations of the eye of the person.

According to further embodiment,
  the system is a two zones lens comprising a central zone and a surrounding zone, where the surrounding zone is adapted to the vision parameters of the person and the central zone is also adapted to the vision parameters of the person and the high order aberrations of the system consisting of the combination of the central zone of the lens and the eye of the person is lower than the high order aberrations of the eye of the person.
  the system is a lens system which consists of a first lens which is adapted to the vision parameters of the person and a second lens which is designed so that the high order aberrations of the system consisting of the combination of the first and second lens of the lens system and the eye of the person is lower than the high order aberrations of the eye of the person.

the second lens is clipable on the first lens.

the system is an optical system which consists of a lens adapted to the vision parameters of the person and an artificial pupil.

The invention also relates to a clipable lens fixable to a lens which is adapted to a person vision parameters to improve the receptiveness of the person to a training session of the human visual system where visual stimuli arrangements are provided to the person and where the clipable lens is designed to obtain high order aberrations of the system consisting of the combination of the clipable lens fixated to the lens adapted to a person vision parameters and the eye of the person which is lower than the high order aberrations of the eye of the person.

The invention relates also to system for identifying deficiencies, inefficiencies, or both, in neuronal interactions of a person's visual cortex, the system comprising:

a) a processor;

b) an image generator coupled to the processor;

c) the processor and image generator configured to generate visual stimuli comprising arrangements of one or more target images, each arrangement being designed to induce a level of neuronal facilitation and/or a level of neuronal suppression in a person's visual cortex, the arrangements comprising a parameter of the one or more target images;

d) an input device coupled to the processor, the input device configured to receive the person's responses to the visual stimuli, the responses indicating detection or discrimination by the person of the one or more target images of the respective arrangements;

e) the processor and image generator configured to generate at least some of the visual stimuli based at least in part upon the person's responses to previous visual stimuli, the at least some visual stimuli designed to induce differing levels of facilitation and levels of neuronal suppression in the person's visual cortex;

f) the processor and image generator being configured to generate sufficient visual stimuli of differing levels of facilitation and levels of neuronal suppression in the person's visual cortex until responses to a sufficient number of facilitations and levels of neuronal suppression levels are received from the person such that deficiencies, inefficiencies, or both, in neuronal interactions of the person's visual cortex may be identified by comparing a function of the person's responses to a normative response function of persons without known vision deficiencies;

g) means provided so that the high order aberrations of the system consisting of the combination of said means and the eye of the person is lower than the high order aberrations of the eye of the person.

The invention also relates to a computer program product comprising one or more stored sequences of instructions that is accessible to a processor and which, when executed by the processor, causes the processor to carry out the steps of the different embodiments of the preceding methods.

The invention also relates to a computer-readable medium carrying one or more sequences of instructions of the preceding computer program product.

Unless specifically stated otherwise, as apparent from the following discussions, it is appreciated that throughout the specification discussions utilizing terms such as "computing", "calculating" "generating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Non limiting embodiments of the invention will now be described with reference to examples and to the accompanying drawings wherein.

DETAILED DESCRIPTION OF THE DRAWINGS

Skilled artisans appreciate that elements in the figures are illustrated for simplicity and clarity and have not necessarily been drawn to scale.

Figure 1:
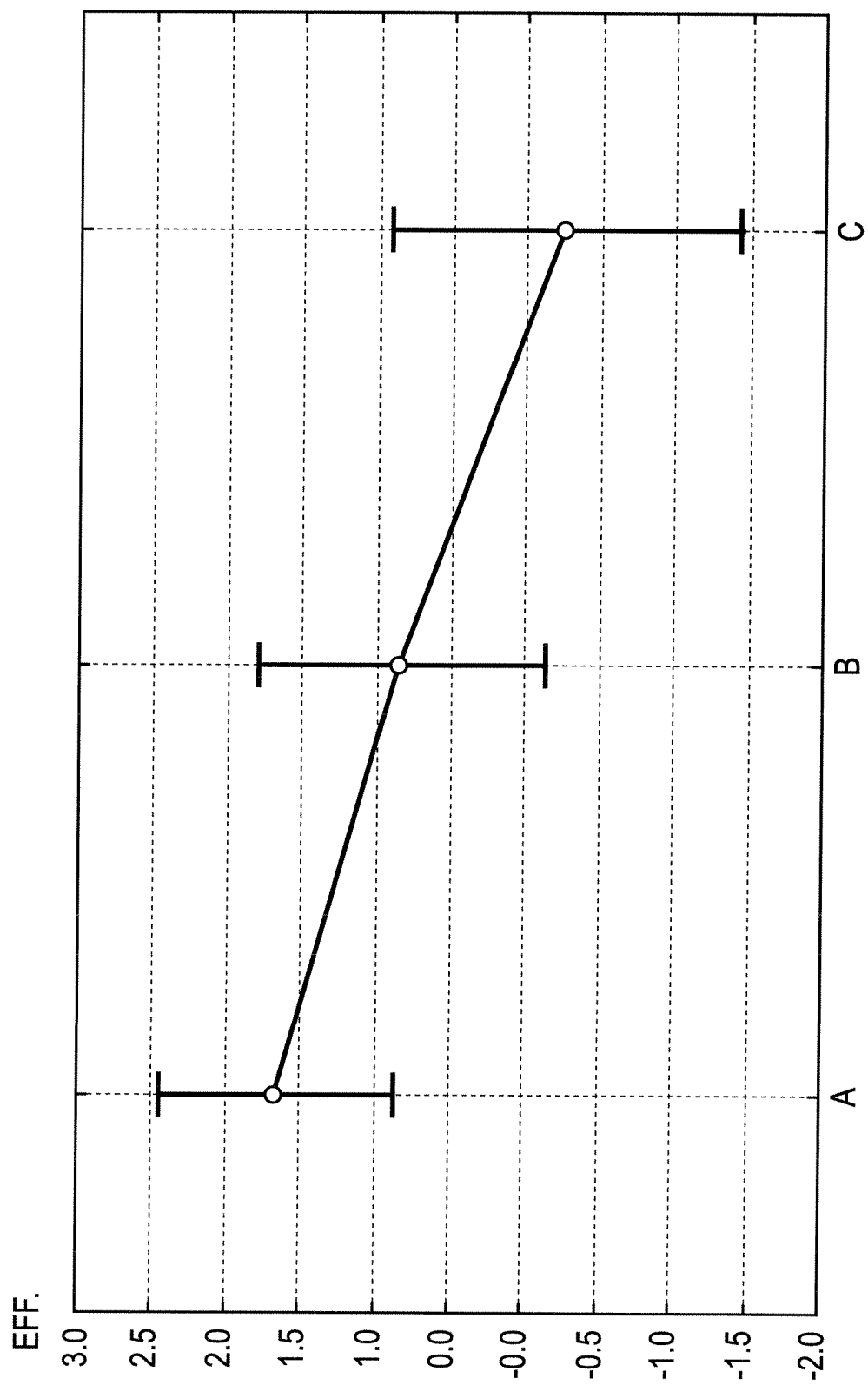
FIG. 1 is a graph of the efficiency of the NeuroVision training method as a function of eye's characteristics of three groups of eyes.

FIG. 1 is the result of a study of the inventors who investigated the variation of the efficiency (EFF) of the NeuroVision method as a function of high order aberrations characteristics of a population of individuals. During this study, the eyes of 19 persons have been characterized and these persons have attended a complete NeuroVision training session.

The inventors have observed that a sensitive parameter is the high order aberrations RMS value of the eye which is dramatically linked to the efficiency of the NeuroVision method. This link is present independently of other sensitive parameters, for example, visual acuity of the subject at the beginning of the training session.

High order aberrations RMS value has been measured using wavefront analysis. An aberrometer is designed to measure the wavefront of the eyes including sphere, cylinder, and the high-order aberrations. Shack-Hartmann aberrometry is known as the most popular way to measure aberrations of the human eye in use today. Commercial ophthalmic Shack-Hartmann aberrometers are for example sold by Wave Front Sciences Inc, VISX, ALCON, Image Eyes (see for example irx3 aberrometer).

Said aberrometers measure the wavefront shape by measuring the distance between the wavefront surface refracted by an eye's optic and a reference plane located in the eye's entrance pupil. This distance is known as the wavefront error. A Shack-Hartmann data set consists of a large array of numbers (wavefront errors) for different position on the pupil plane. As a whole, the entire data set is called the wavefront.

The wavefront can be analysed using Zernike polynomials. Such an analysis is for example recommended by the Optical Society of America (OSA) for describing ocular wavefront aberrations, but other polynomials, such as for example Taylor series or splines can also be used to mathematically describe a wavefront.

The Zernike expansion presents the aberrations in an orthogonal set of polynomials. It can be displayed in the form of a pyramid. Vertically each row represents a typical form of aberration; these are called (radial) orders. The top is called the zero order, which actually is no aberration but a constant that can be added for e.g. scaling. The second row (the first order) represents prismatic effects. Each presentation of an aberration is called a term. Also this starts at the top with the zero term. The prismatic effects are based vertical (Z-term 2, up or down) and horizontal (Z-term 3, in or out). Since the zero and first orders (Z-terms 1-3) are linked to specific visual defects, or to specific measurement conditions, these are usually not pictured. It starts to become interesting as of the second order. In the middle of the pyramid, defocus (Z-term 4) can be found. It is placed at the axis line of the pyramid. This is because defocus (spherical part of a refraction) is rotational symmetric (zero angular frequency). On both sides of defocus, the astigmatic (cylinder in the refraction) terms Z-3 and Z-5 can be found. These are special conditions of defocus because they work in one meridian only. Consequently these must be indicated with a direction (axis of the cylinder), Z-3 for oblique astigmatism and Z-5 for horizontal astigmatism. The third order aberrations include coma and trefoil, each has a direction, so no Z-term in this row at the middle. Next are 5 terms of the $4^{th}$ order. Spherical aberrations (Z-12) is rotational symmetric, the other terms (with a direction) are secondary astigmatism and tetra foil. For describing aberrations in optics the pyramid continues with many more orders and terms. Usually these are in the eye not present or very low. Even within the 14 Z-terms as discussed not all terms are of equal importance to the eye. For the eye the second order aberrations are called "low order aberrations" and include the sphere and cylinder value of the refraction. Third and higher orders are called "high order aberrations".

A high order aberrations Root Mean Square (RMS) value can then, for example, be calculated using the Zernike polynomials components values of the wavefront aberrations function, which order is equal or higher than 3.

In order to compare high order aberrations RMS values of different eyes, it is useful to normalize said RMS value according to a reference eye.

The inventors have chosen to normalize the measured RMS values according to a 3.5 mm diameter pupil. Each person has been characterized by the HO_RMS (high order aberrations RMS value) mean value of both eyes. Wavefront of each eye of the person have been measured. Classically, on the softwares linked to the wavefront, the RMS (Root-Mean Square) of the wave-front is calculated on a specified diameter which is smaller that the pupil diameter. The following calculating method has been used:

Fit a Zernike polynomial of the wavefront limited to the given diameter;

Calculate the RMS of high order aberrations of this Zernike polynomial;

Results are HO_RMS_re for the right eye, and HO_RMS_le for the left eye.

For each person, HO_RMS is calculated:

HO_RMS=(HO_RMS_re+HO_RMS_le)/2

The common unit of aberrations values is μm (micrometer).

The inventors have characterized the 19 mentioned persons using a Zernike polynomials analysis of wavefront aberrations functions measured with a Shack-Hartmann aberrometer and normalized said results for a 3.5 mm pupil. Then, the inventors have characterized each of the 19 subjects that have participated to the training sessions, by the HO_RMS values of the measured eyes. The HO_RMS range was between 0.07 and 0.16 microns.

The efficiency of the NeuroVision method has been determined for each participant to the training session, by the following method:

"Efficiency factor for Visual Acuity", "efficiency factor for Contrast Sensitivity", and "efficiency factor for psychological feeling" have been defined and calculated. All of these factors vary between −1 and +1.

An "efficiency of the training session" is defined as the sum of each efficiency factor. It can vary between −3 and +3.

Definition of the "Efficiency Factor for Visual Acuity", Eff_VA:

Eff_VA=1 if Delta_VA_HC$\leq$−0.12 LogMar and Delta_VA_LC<−0.12 LogMar

Eff_VA=−1 if Delta_VA_HC$\geq$−0.06 LogMar and Delta_VA_LC$\geq$−0.08 LogMar

Eff_VA=0 in the other cases where:

LogMar is the logarithm of the minimum angle of resolution which is a commonly used scale in the field of optometry and opthalmology; the use of LogMar allows analysis of visual acuity scores effectively and comparisons of results can be made precisely. The equal linear steps of the LogMar scale represent equal ratios in standard size sequence;

and where:

Delta_VA_HC=VA_HC_end−VA_HC_beg,

VA_HC_end=Visual Acuity in High Contrast one day after the end of the training session VA_HC_beg=Visual Acuity in High Contrast one day before the beginning of the training session VA_LC_end=Visual Acuity in Low Contrast one day after the end of the training session VA_LC_beg=Visual Acuity in Low Contrast one day before the beginning of the training session The VA measurements are done binocularly.

The VA measurements are done in the same conditions at the beginning and at the end: same luminous conditions of the room, same hour of the day (for example in the morning where no strain nor eyestrain of the person occur)

Definition of the "Efficiency Factor for Contrast Sensitivity", Eff_SC:

Eff_SC=1 if Delta_SC$\geq$0.9

Eff_SC=−1 if Delta_SC<0.7

Eff_SC=0 in the other cases,

Where: Delta_SC=mean (Delta_SC_1.5; Delta_SC_3.0; Delta_SC_6.0; Delta_SC_12.0; Delta_SC_18.0)

Where:

Delta_SC_1.5=mean (Delta_SC_1.5_re; Delta_SC_1.5_le)

Delta_SC_3.0=mean (Delta_SC_3.0_re; Delta_SC_3.0_le)

Delta_SC_6.0=mean (Delta_SC_6.0_re; Delta_SC_6.0_le)

Delta_SC_12.0=mean (Delta_SC_12.0_re; Delta_SC_12.0_le)

Delta_SC_18.0=mean (Delta_SC_18.0_re; Delta_SC_18.0_le)

Where "_re" means right eye and "_le" means left eye.

and where, for each eye, following parameters are defined:

Delta_SC_1.5=SC_1.5_end−SC_1.5_beg (Spatial frequency=1.5 cycles by degree)

Delta_SC_3.0=SC_3.0_end−SC_3.0_beg (Spatial frequency=3.0 cycles by degree)

Delta_SC_6.0=SC_6.0_end−SC_6.0_beg (Spatial frequency=6.0 cycles by degree)

Delta_SC_12.0=SC_12.0_end−SC_12.0_beg (Spatial frequency=12.0 cycles by degree)

Delta_SC_18.0=SC_18.0_end−SC_18.0_beg (Spatial frequency=18.0 cycles by degree)

SC_value is equal to the number of correctly detected target for each spatial frequency.

The SC measurements are made eye by eye. The chart used is the FACT 101 Near Point Test, from STEREO OPTICAL CO.

Definition of the "Efficiency Factor for psychological feeling", Eff_psycho:

At the end of the training session, the participant fills in a questionnaire, and, in particular, answers to a question concerning the satisfaction of the training session:

"Taking into account the effort and the results of the training session, what is your degree of satisfaction?"

Three possible answers are submitted: "not satisfied", "satisfied", "no opinion".

Eff_psycho=1 if "satisfied"

Eff_psycho=−1 if "not satisfied"

Eff_psycho=0 if "no response" or "no opinion"

As previously said:

EFF=Eff_VA+Eff_SC+Eff_psycho

According to the present experiments, the target for the NeuroVision tests was approximately 20 mm large and distant of 1.50 m from the eye. The inventors have analysed the data and surprisingly identified that the efficiency of the NeuroVision method is highly dependant of the HO_RMS values of the persons.

They classified the HO_RMS values in three populations:
population A, where the HO_RMS values are equal or less than 0.10 μm,
population B, where the HO_RMS values are more than 0.10 μm and equal or less than 0.14 μm,
population C, where the HO_RMS values are more than 0.14 μm.

The efficiency (EFF) of the NeuroVision method is shown on FIG. 1 for the three eye populations A, B and C. It has to be understood that the efficiency of the NeuroVision method is very good when EFF is equal or greater than 2 and excellent when EFF is equal to about 3. This efficiency is medium or low when EFF is between 0 and 1 and it is even negative (risk of visual deterioration, or dissatisfaction) when EFF is negative.

Vertical bars on FIG. 1 represent the confidence intervals calculated at 95 percent.

According to the present invention, the inventors have discovered that the efficiency of the NeuroVision method can be increased when decreasing the HO_RMS value of an eye, thus by providing means to obtain a high order aberrations RMS value of the system consisting of said means combined with the eye of the person to be trained which is lower than the high order aberrations RMS value of the eye of the person.

Every known means to obtain a high order aberrations RMS value of the system consisting of said means combined with the eye of the person to be trained which is lower than the high order aberrations RMS value of the eye of the person, can be used in the present invention.

Figure 2:
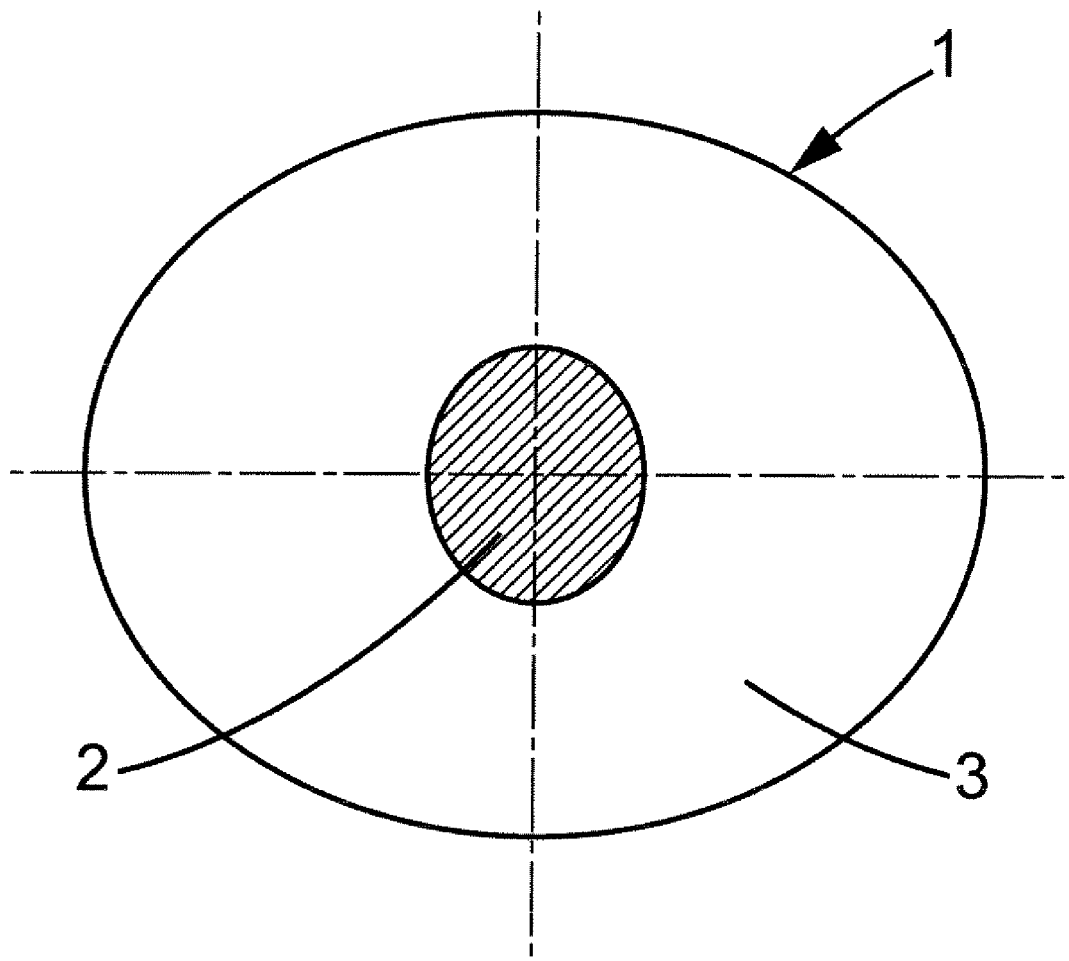
FIG. 2 is a view of a surface of a lens system according to the present invention.

For example, such means can be a lens system. Such lens system may be a two zones lens as shown on FIG. 2. The lens 1 comprises a central zone 2 and a surrounding zone 3. The surrounding zone 3 is adapted to the standard vision parameters of the eye of the person to be trained, i.e. the aberrations order equal or less to 2, and to the training protocol. The central zone 2 is designed to be adapted to the vision parameters and the training protocol, but also to lower the high order aberrations RMS value of the person to be trained. The central zone 2 is designed so as its surface corresponds substantially to the eye pupil, when the eye is in the direction of the visual stimuli. This zone 2 is designed so as to be placed in front of the pupil of the person when he or she is viewing a far distance scene. The resulting high order aberrations RMS value of the system consisting of said lens 1 and the eye of the person is preferably equal or less than 0.14 μm, and for example equal or less than 0.10 μm for a normalized pupil of 3.5 mm. It may be advantageous to obtain a RMS value less than 0.10 microns.

An example of calculation of a compensated lens is the following:

An optimization software for example CODE V, or other optimization software can be used, that can function with mean-square error minimization.

The optical system is firstly defined.

The eye can be considered as a Wavefront (the measured wavefront), in the entering pupil of the eye. The compensating lens is to be placed at the right position. The compensating lens can be modelized by Zernike polynomials of an order sufficiently high to generate high order aberrations.

Ray tracing can be used where a light beam without aberrations comes from a point, situated at the same position as the real stimulus of the real training session. The Wavefront coming in the eye is then calculated after having passed through the lens and the Wavefront of the eye.

The optimization consists in finding the RMS minimum for the resulting wavefront, by varying the Zernike coefficients of the compensating lens.

This method of optimization is currently used by the skilled in the art.

Such lenses can be for example worn using training spectacles, such as for example the training spectacles described in French patent, FR 2 503 559.

Optical lenses to correct optical aberrations of the third and fourth orders of an eye, such described in French patent FR 2 868 170 are also suitable as a lens system used to improve the receptiveness of a person according to the present invention.

Following another embodiment the person to be trained keeps his own corrective glasses and a lens or more is added to his glasses to obtain a high order aberrations RMS value of the system consisting of his glasses, the added lens and the eye of the person to be trained which is lower than the high order aberrations RMS value of the eye of the person.

Such a lens may for example be added in front of the person's spectacles, and can be a clipable lens such as a monocular shield described in European patent EP 0 965 063 or using any of the clips for clipable lens commercialized by the company "Color Clip".

The clipable lens comprises for example a central zone according to preceding embodiment and a surrounding zone without any optical correction.

Following another embodiment the system to obtain a high order aberrations RMS value of the system consisting of said means combined with the eye of the person to be trained which is lower than the high order aberrations RMS value of the eye of the person consists of an optical system comprising at least an adaptive mirror, which is conjugated with the eye pupil, in order to compensate the aberrations of the eye. An example of such a device is the system crx1™ Adaptive Optics Visual Simulator, commercialized by the Company Imagine Eyes.

Following another embodiment the system to obtain a high order aberrations RMS value of the system consisting of said means combined with the eye of the person to be trained which is lower than the high order aberrations RMS value of the eye of the person consists of an ophthalmic contact lens that corrects the high order aberrations, for example the contact lens as disclosed in U.S. Pat. No. 6,379,008.

Following another embodiment the system to obtain a high order aberrations RMS value of the system consisting of said means combined with the eye of the person to be trained which is lower than the high order aberrations RMS value of the eye of the person consists of a lens adapted to the vision parameters of the person, and to the training protocol, and an artificial pupil disposed on said lens. An "artificial pupil" is known as being a diaphragm of specified diameter. It is used to limit the quantity of light entering into the eye. Such an artificial pupil can be placed at a conjugated plane of the pupil of an eye.

This embodiment is due to the fact that we know that the quality of the image arriving to the retina is linked to the quality of the wavefront (RMS), but also to the diameter of the pupil of the eye.

The artificial pupil can be fixated, for example, on frames or on trial frames.

The diameter of the artificial pupil must be littler than the natural diameter of the eye pupil, in the luminous conditions of the training session. On an example of realisation of the invention, the diameter of the artificial pupil can be comprised between 2 and 3.5 mm.

In this last case, the HO_RMS is directly equal to the RMS of the wavefront measured on the diameter of the artificial pupil. This artificial pupil can be fixated, for example, on frames or on trial frames.

As for an example, artificial pupils have been provided to several persons of group C and the high order aberrations the RMS values of the system consisting of their eye, a lens adapted to their vision parameter and an artificial pupil of different diameter have been determined and are reported in following table:

| Diameter of the artificial pupil (mm) | 3.5 | 3.2 | 3 |
|---|---|---|---|
| High order aberrations (μm) RMS value of the system | 0.15 | 0.12 | 0.10 |

It has to be noted that the preceding lens systems used to improve the receptiveness of a person may be substituted by other means, such as for example calculation means which could take into account the high order aberrations value correction in the images which are shown to the person during the training method.

After having provided means to lower the high order aberrations RMS values of the system comprising said means combined with the eye(s) of the person to be trained which is lower than the high order aberrations RMS value of his eye(s), the method for identifying deficiencies, inefficiencies or both, in neuronal interactions of a person's visual cortex is implemented according to known methods, such as for example the method of U.S. Pat. No. 7,004,912 or U.S. Pat. No. 6,876,758. Other methods, such as described in PCT patent applications WO 2005/044096, WO 2006/025056 or WO 2007/043047 can also be improved using the present invention.

The systems used to implement corresponding training method are described in the previous documents.

It has to be understood that the teaching drawn from the present experiments based on high order aberrations RMS (Root Mean Square) values are transposable to other parameters known in the state of the art which are characteristic of the high order aberrations of an optical system such as for example "Strehl Ratio" or "Pupil Ratio".

The invention has been described above with the aid of embodiments without limitation of the general inventive concept which is evident from the claims and the general portion of the specification.

The invention claimed is:

1. A method to improve the receptiveness of a person to a training session of the human visual system where at least one visual stimuli arrangement is provided to the person, the method comprising the steps of:
   (a) measuring high order aberrations of at least one eye of the person;
   (b) calculating a parameter which is characteristic of the high order aberrations of an optical system with the data of step (a);
   (c) providing means so that the high order aberrations of the system consisting of the combination of said means and the eye of the person is lower than the high order aberrations of the eye of the person,
   wherein said provided means are not configured to correct the high order aberrations of the eye of the person.

2. The method of claim 1, wherein at least one visual stimuli arrangement is designed to modify levels of neuronal facilitation and/or levels of neuronal suppression in the person's visual cortex.

3. The method of claim 1, wherein the parameter which is characteristic of the high order aberrations of an optical system is chosen in the list consisting of the high order aberrations RMS (Root Mean Square) value, the Strehl Ratio, the Pupil Ratio.

4. The method of claim 3, wherein the parameter which is characteristic of the high order aberrations of an optical system is the high order aberrations RMS (Root Mean Square) value, the value of this parameter for the system consisting of the combination of the means and the eye of the person is lower than the value of this parameter for the eye of the person.

5. The method of claim 4 wherein aberrations are calculated using Zernike polynomials analysis and the high order aberrations RMS is calculated for orders equal or greater to the third order.

6. The method of claim 5, wherein the RMS value of the system consisting of means of step (c) combined with the eye of the person is equal or less to 0.14 μm, and for example equal or less to 0.10 μm for a normalized pupil of 3.5 mm.

7. The method of claim 1, wherein the means which are provided at step (c) are an optical system to be worn by the person to be trained.

8. The method according to claim 7, wherein the optical system is a two zones lens comprising a central zone and a surrounding zone, where the surrounding zone is adapted to the vision parameters of the person and the central zone is also adapted to the vision parameters of the person and the high order aberrations of the system consisting of the combination of the central zone of the lens and the eye of the person is lower than the high order aberrations of the eye of the person.

9. The method according to claim 7 wherein the optical system consists of a first lens which is adapted to the vision parameters of the person and a second lens which is designed so that the high order aberrations of the system consisting of the combination of the first and second lens of the lens system and the eye of the person is lower than the high order aberrations of the eye of the person.

10. The method according to claim 9 wherein the second lens is clipable on the first lens.

11. The method according to claim 7 wherein the optical system consists of a lens which is adapted to the vision parameters of the person and an artificial pupil disposed on said lens.

12. The method according to claim 1, wherein each visual stimuli arrangement comprises one or more target images each flanked by a pair of flanking images.

13. A non-transitory computer program product comprising one or more stored sequence of instruction that is accessible to a processor and which, when executed by the processor, causes the processor to carry out the steps of claim 1.

14. A non-transitory computer-readable medium carrying one or more sequences of instructions of the computer program product of claim 13.

15. A method for identifying deficiencies, inefficiencies, or both, in neuronal interactions of a person's visual cortex, the method comprising:
   (a1) measuring high order aberrations of at least one eye of the person;
   (a2) calculating a parameter which is characteristic of the high order aberrations of an optical system with the data of step (a1);
   (a3) providing means so that the high order aberrations of the system consisting of the combination of said means and the eye of the person is lower than the high order aberrations of the eye of the person, wherein said provided means are not configured to correct the high order aberrations of the eye of the person;
   (b) providing to the person visual stimuli comprising an arrangement of one or more target images where the arrangement is designed to induce a level of neuronal facilitation and/or levels of neuronal suppression in the person's visual cortex;
   (c) receiving from the person a response to the visual stimuli provided in step (b) the response indicating detection or discrimination by the person of the one or more target images; and
   (d) providing further visual stimuli to the person based at least in part on the response received in step (c) the further visual stimuli comprising a further arrangement of one or more target images designed to induce a different level of facilitation and/or levels of neuronal suppression in the person's visual cortex than the visual stimuli provided in step (b); said step (b)-(d) being repeated until responses to a sufficient number of facilitation and/or levels of neuronal suppression levels are received from the person such that deficiencies, inefficiencies, or both, in neuronal interactions of the person's visual cortex may be identified by comparing a function of the person's responses to a normative response function of persons without known vision deficiencies.

16. The method of claim 15, further comprising providing to the person one or more training sessions of the human visual system including:
   (e) providing to the person visual stimuli arrangements, each arrangement comprising one or more target images designed to modify levels of neuronal facilitation and/or levels of neuronal suppression in the person's visual cortex;
   (f) receiving responses from the person indicating detection or discrimination of the target images in the respective visual stimuli arrangements;
   (g) comparing the person's responses with prior response received from the person to the same or similar visual stimuli arrangements; and
   (h) repeating steps (e)-(g), the visual stimuli arrangements provided in each step (e) based at least partly on results of the preceding comparison step (g) until a sufficient number of responses are received from the person so that improvement in deficiencies, inefficiencies, or both, in neuronal interactions of the person's visual cortex may be identified by comparing a function of the person's responses to a normative response function of persons without known vision deficiencies.

17. The method of claim 15, wherein the target images of steps (b) or (d) or (e) are each flanked by one or more flanking images of similar configuration as the respective target image, and the arrangement comprises a parameter of the one or more target images and the respective flanking images.

18. A non-transitory computer program product comprising one or more stored sequence of instruction that is accessible to a processor and which, when executed by the processor, causes the processor to carry out the steps of claim 15.

19. A non-transitory computer-readable medium carrying one or more sequences of instructions of the computer program product of claim 18.

20. A system to improve the receptiveness of a person to a training session of the human visual system where at least one visual stimuli arrangement is provided to the person, and where the system comprises means designed so that the high order aberrations of the system consisting of the combination of the means and the eye of the person is lower than the high order aberrations of the eye of the person,
   wherein said system is not configured to correct the high order aberrations of the eye of the person; and
   wherein the system comprises a two zones lens having a central zone and a surrounding zone, where the surrounding zone is adapted to the vision parameters of the person and the central zone is also adapted to the vision parameters of the person and the high order aberrations of the system consisting of the combination of the central zone of the lens and the eye of the person is lower than the high order aberrations of the eye of the person.

21. The system of claim 20 wherein the system is a lens system which consists of a first lens which is adapted to the vision parameters of the person and a second lens which is designed so that the high order aberrations of the system consisting of the combination of the first and second lens of the lens system and the eye of the person is lower than the high order aberrations of the eye of the person.

22. The lens system according to claim 21 wherein the second lens is clipable on the first lens.

23. The system according to claim 20 wherein the system is an optical system which consists of a lens adapted to the vision parameters of the person and an artificial pupil.

24. The system of claim 20 suitable for identifying deficiencies, inefficiencies, or both, in neuronal interactions of a person's visual cortex, the system comprising:
   a) a processor,
   b) an image generator coupled to the processor,
   c) the processor and image generator configured to generate visual stimuli comprising arrangements of one or more target images, each arrangement being designed to induce a level of neuronal facilitation and/or a level of neuronal suppression in a person's visual cortex, the arrangements comprising a parameter of the one or more target images;
   d) an input device coupled to the processor, the input device configured to receive the person's responses to the visual stimuli, the responses indicating detection or discrimination by the person of the one or more target images of the respective arrangements;
   e) the processor and image generator configured to generate at least some of the visual stimuli based at least in part upon the person's responses to previous visual stimuli, the at least some visual stimuli designed to induce differing levels of facilitation and levels of neuronal suppression in the person's visual cortex;
   f) the processor and image generator being configured to generate sufficient visual stimuli of differing levels of facilitation and levels of neuronal suppression in the person's visual cortex until responses to a sufficient number of facilitations and levels of neuronal suppression levels are received from the person such that deficiencies, inefficiencies, or both, in neuronal interactions of the person's visual cortex may be identified by comparing a function of the person's responses to a normative response function of persons without known vision deficiencies;
   g) means provided so that the high order aberrations of the system consisting of the combination of said means and the eye of the person is lower than the high order aberrations of the eye of the person.

25. A clipable lens fixable to a lens which is adapted to a person vision parameters to improve the receptiveness of the person to a training session of the human visual system where visual stimuli arrangements are provided to the person and where the clipable lens is designed to obtain high order aberrations of the system consisting of the combination of the clipable lens fixated to the lens adapted to a person vision parameters and the eye of the person which is lower than the high order aberrations of the eye of the person, wherein said clipable lens is not configured to correct the high order aberrations of the eye of the person.

* * * * *